United States Patent
Gunaratnam

(10) Patent No.: US 6,973,929 B2
(45) Date of Patent: *Dec. 13, 2005

(54) FOREHEAD SUPPORT FOR A FACIAL MASK

(75) Inventor: Michael K. Gunaratnam, Marsfield (AU)

(73) Assignee: ResMed Limited, North Ryde (AU)

( * ) Notice: Subject to any disclaimer, the term of this patent is extended or adjusted under 35 U.S.C. 154(b) by 0 days.

This patent is subject to a terminal disclaimer.

(21) Appl. No.: 10/320,701

(22) Filed: Dec. 17, 2002

(65) Prior Publication Data

US 2003/0084904 A1 May 8, 2003

Related U.S. Application Data

(63) Continuation of application No. 09/538,349, filed on Mar. 29, 2000, now Pat. No. 6,520,182.

(30) Foreign Application Priority Data

Mar. 29, 1999 (AU) .............................................. PP9499

(51) Int. Cl.⁷ ............................................. A62B 18/08
(52) U.S. Cl. ............................. 128/207.11; 128/206.27; 128/207.17
(58) Field of Search ....................... 128/207.11, 206.27, 128/201.11, 206.24, 206.23, 207.17, 207.13, DIG. 26, 200.27, 206.28, 201.22, 201.23, 201.24, 201.29; 15/236.03, 248.2, 262; 427/260; 606/174, 205

(56) References Cited

U.S. PATENT DOCUMENTS

| 781,516 A | 1/1905 | Guthrie |
| 812,706 A | 2/1906 | Warbasse |
| 1,081,745 A | 12/1913 | Johnston et al. |
| 1,192,186 A | 7/1916 | Greene |
| 1,653,572 A | 12/1927 | Jackson |
| 1,926,027 A | 9/1933 | Biggs |
| 2,123,353 A | 7/1938 | Catt |
| 2,245,969 A | 6/1941 | Francisco et al. |
| 2,248,477 A | 7/1941 | Lombard |
| 2,254,854 A | 9/1941 | O'Connell |
| 2,317,608 A | 4/1943 | Heidbrink |
| 2,371,965 A | 3/1945 | Lehmberg |
| 2,376,671 A | 5/1945 | Fink |
| 2,415,846 A | 2/1947 | Randall |
| 2,438,058 A | 3/1948 | Kincheloe |
| 2,578,621 A | 12/1951 | Yant |

(Continued)

FOREIGN PATENT DOCUMENTS

| AU | 91/77110 B | 11/1991 |
| AU | 94/64816 B | 12/1994 |

(Continued)

OTHER PUBLICATIONS

Product Brochure for ResMed "Sullivan® Mirage™—The Mirage is Real. A Perfect Fit—First Time," ©1997 ResMed Limited, 4, pages.

(Continued)

*Primary Examiner*—Henry Bennett
*Assistant Examiner*—Mital Patel
(74) *Attorney, Agent, or Firm*—Nixon & Vanderhye P.C.

(57) ABSTRACT

A forehead support (10) for a respiratory mask (14). The forehead support (10) includes a pair of arms (22). The arms (22) are each adapted to locate a forehead cushion (30). The arms (22) are also adapted to pivot relative to each other. The arms (22) are also selectively lockable at two or more angular positions relative to each other. The forehead support (10) can thus be adjusted to suit the facial topography of the wearer of the respiratory mask (14).

15 Claims, 11 Drawing Sheets

U.S. PATENT DOCUMENTS

| | | |
|---|---|---|
| 2,590,006 A | 3/1952 | Gordon |
| 2,931,356 A | 4/1960 | Schwarz |
| D188,084 S | 5/1960 | Garelick |
| 2,939,458 A | 6/1960 | Lundquist |
| 3,013,556 A | 12/1961 | Galleher |
| 3,182,659 A | 5/1965 | Blount et al. |
| 3,189,027 A | 6/1965 | Bartlett |
| 3,193,624 A | 7/1965 | Webb et al. |
| 3,238,943 A | 3/1966 | Holley |
| 3,315,674 A | 4/1967 | Bloom et al. |
| 3,330,273 A | 7/1967 | Bennett |
| 3,362,420 A | 1/1968 | Blackburn et al. |
| 3,363,833 A | 1/1968 | Laerdal |
| 3,556,122 A | 1/1971 | Laerdal |
| 3,580,051 A | 5/1971 | Blevins |
| 3,700,000 A | 10/1972 | Hesse et al. |
| 3,720,235 A | 3/1973 | Schrock |
| 3,750,333 A | 8/1973 | Vance |
| 3,752,157 A | 8/1973 | Malmin |
| 3,796,216 A | 3/1974 | Schwarz |
| 3,799,164 A | 3/1974 | Rollins |
| D231,803 S | 6/1974 | Huddy |
| 3,830,230 A | 8/1974 | Chester |
| 4,077,404 A | 3/1978 | Elam |
| D250,131 S | 10/1978 | Lewis et al. |
| 4,120,302 A | 10/1978 | Ziegler |
| 4,167,185 A | 9/1979 | Lewis |
| 4,226,234 A | 10/1980 | Gunderson |
| 4,245,632 A | 1/1981 | Houston |
| D262,322 S | 12/1981 | Mizerak |
| 4,304,229 A | 12/1981 | Curtin |
| 4,328,797 A | 5/1982 | Rollins et al. |
| 4,347,205 A | 8/1982 | Stewart |
| 4,354,488 A | 10/1982 | Bartos |
| 4,402,316 A | 9/1983 | Gadberry |
| 4,412,537 A | 11/1983 | Tiger |
| 4,467,799 A | 8/1984 | Steinberg |
| 4,522,639 A | 6/1985 | Ansite et al. |
| 4,558,710 A | 12/1985 | Eichler |
| 4,616,647 A | 10/1986 | McCreadie |
| 4,622,964 A | 11/1986 | Flynn |
| 4,655,213 A | 4/1987 | Rapoport et al. |
| 4,665,570 A | 5/1987 | Davis |
| 4,671,271 A | 6/1987 | Bishop et al. |
| 4,677,975 A | 7/1987 | Edgar et al. |
| 4,677,977 A | 7/1987 | Wilcox |
| D293,613 S | 1/1988 | Wingler |
| 4,739,755 A | 4/1988 | White et al. |
| 4,770,169 A | 9/1988 | Schmoegner et al. |
| 4,774,941 A | 10/1988 | Cook |
| 4,782,832 A | 11/1988 | Trimble et al. |
| 4,799,477 A | 1/1989 | Lewis |
| 4,809,692 A | 3/1989 | Nowacki et al. |
| 4,819,629 A | 4/1989 | Jonson |
| 4,821,713 A | 4/1989 | Bauman |
| 4,841,953 A | 6/1989 | Dodrill |
| 4,848,334 A | 7/1989 | Bellm |
| 4,848,366 A | 7/1989 | Aita et al. |
| 4,907,584 A | 3/1990 | McGinnis |
| 4,910,806 A | 3/1990 | Baker et al. |
| 4,919,128 A | 4/1990 | Kopala et al. |
| 4,938,210 A | 7/1990 | Shene |
| 4,938,212 A | 7/1990 | Snook et al. |
| 4,944,310 A | 7/1990 | Sullivan |
| D310,431 S | 9/1990 | Bellm |
| 4,971,051 A | 11/1990 | Toffolon |
| 4,986,269 A | 1/1991 | Hakkinen |
| 4,989,596 A | 2/1991 | Macris et al. |
| 4,989,599 A | 2/1991 | Carter |
| 5,005,568 A | 4/1991 | Loescher et al. |
| 5,005,571 A | 4/1991 | Dietz |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,063,922 A | 11/1991 | Hakkinen |
| 5,069,205 A | 12/1991 | Urso |
| D323,908 S | 2/1992 | Hollister et al. |
| 5,109,839 A | 5/1992 | Blasdell et al. |
| 5,109,840 A | 5/1992 | Daleiden |
| 5,121,745 A | 6/1992 | Israel |
| 5,133,347 A | 7/1992 | Huennebeck |
| 5,140,980 A | 8/1992 | Haughey et al. |
| 5,140,982 A | 8/1992 | Bauman |
| 5,159,938 A | 11/1992 | Laughlin |
| 5,178,138 A | 1/1993 | Walstrom et al. |
| D334,633 S | 4/1993 | Rudolph |
| 5,220,699 A | 6/1993 | Farris |
| 5,231,983 A | 8/1993 | Matson et al. |
| 5,233,978 A | 8/1993 | Callaway |
| 5,243,971 A | 9/1993 | Sullivan et al. |
| 5,265,595 A | 11/1993 | Rudolph |
| 5,279,289 A | 1/1994 | Kirk |
| 5,280,784 A | 1/1994 | Kohler |
| 5,311,862 A | 5/1994 | Blasdell et al. |
| 5,322,057 A | 6/1994 | Raabe et al. |
| 5,343,878 A | 9/1994 | Scarberry et al. |
| 5,357,951 A | 10/1994 | Ratner |
| 5,372,130 A | 12/1994 | Stern et al. |
| 5,388,571 A | 2/1995 | Roberts et al. |
| 5,404,871 A | 4/1995 | Goodman et al. |
| 5,419,318 A | 5/1995 | Tayebi |
| 5,429,126 A | 7/1995 | Bracken |
| 5,429,683 A | 7/1995 | Le Mitouard |
| 5,431,158 A | 7/1995 | Tirotta |
| 5,438,981 A | 8/1995 | Starr et al. |
| 5,441,046 A | 8/1995 | Starr et al. |
| D362,061 S | 9/1995 | McGinnis et al. |
| 5,477,852 A | 12/1995 | Landis et al. |
| 5,479,920 A | 1/1996 | Piper et al. |
| 5,481,763 A | 1/1996 | Brostrom et al. |
| 5,488,948 A | 2/1996 | Dubruille et al. |
| 5,492,116 A | 2/1996 | Scarberry et al. |
| 5,501,214 A | 3/1996 | Sabo |
| 5,509,404 A | 4/1996 | Lloyd et al. |
| 5,517,986 A | 5/1996 | Starr et al. |
| 5,538,000 A | 7/1996 | Rudolph |
| 5,540,223 A | 7/1996 | Starr et al. |
| 5,542,128 A | 8/1996 | Lomas |
| 5,546,936 A | 8/1996 | Virag et al. |
| 5,558,090 A | 9/1996 | James |
| RE35,339 E | 10/1996 | Rapoport |
| 5,560,354 A | 10/1996 | Berthon-Jones et al. |
| 5,570,682 A | 11/1996 | Johnson |
| 5,570,689 A | 11/1996 | Starr et al. |
| D377,089 S | 12/1996 | Starr et al. |
| 5,592,938 A | 1/1997 | Scarberry et al. |
| 5,608,647 A | 3/1997 | Rubsamen et al. |
| 5,642,730 A | 7/1997 | Baran |
| 5,647,355 A | 7/1997 | Starr et al. |
| 5,647,357 A | 7/1997 | Barnett et al. |
| 5,649,532 A | 7/1997 | Griffiths |
| 5,649,533 A | 7/1997 | Oren |
| 5,655,520 A | 8/1997 | Howe et al. |
| 5,655,527 A | 8/1997 | Scarberry et al. |
| 5,657,493 A | 8/1997 | Ferrero et al. |
| 5,657,752 A | 8/1997 | Landis et al. |
| 5,662,101 A | 9/1997 | Ogden et al. |
| 5,666,946 A | 9/1997 | Langenback |
| 5,685,296 A | 11/1997 | Zdrojkowski et al. |
| 5,687,715 A | 11/1997 | Landis et al. |

| | | | |
|---|---|---|---|
| 5,715,814 A | 2/1998 | Ebers | |
| 5,746,201 A | 5/1998 | Kidd | |
| 5,813,423 A | 9/1998 | Kirchgeorg | |
| 5,832,918 A | 11/1998 | Pantino | |
| 6,044,844 A | 4/2000 | Kwok et al. | |
| 6,119,693 A | 9/2000 | Kwok et al. | |
| 6,463,931 B1 | 10/2002 | Kwok et al. | |
| 6,520,182 B1 * | 2/2003 | Gunaratnam | 128/206.27 |

FOREIGN PATENT DOCUMENTS

| | | |
|---|---|---|
| AU | 95/16178 B | 7/1995 |
| AU | A 32914/95 | 2/1996 |
| AU | 9459430 | 2/1996 |
| AU | A 41018/97 | 4/1998 |
| AU | A 89312/98 | 1/1999 |
| CA | 1039144 | 9/1928 |
| DE | 459 104 | 4/1928 |
| DE | 701 690 | 1/1941 |
| DE | 159396 | 6/1981 |
| DE | 3015279 A1 | 10/1981 |
| DE | 3345067 A1 | 6/1984 |
| DE | 3537507 | 4/1987 |
| DE | 3539073 A1 | 5/1987 |
| DE | 4004157 C1 | 4/1991 |
| DE | 4343205 A1 | 6/1995 |
| DE | 197 35 359 | 1/1998 |
| DE | 297 23 101 | 7/1998 |
| DE | 298 10846 U1 | 8/1998 |
| EP | 0 054 154 | 10/1981 |
| EP | 0 252 052 A1 | 1/1988 |
| EP | 0 264 772 A1 | 4/1988 |
| EP | 0 386 605 A1 | 2/1990 |
| EP | 0427474 A2 | 5/1991 |
| EP | 0 462 701 A1 | 12/1991 |
| EP | 0 602 424 | 11/1993 |
| EP | 0 608 684 A1 | 8/1994 |
| EP | 0 0697 225 | 7/1995 |
| EP | 178 925 A2 | 4/1996 |
| EP | 0 747 078 A2 | 12/1996 |
| EP | 0 821 978 | 2/1998 |
| FR | 2 574 657 A1 | 6/1986 |
| FR | 2 658 725 A1 | 8/1991 |
| FR | 2 749 176 | 12/1997 |
| GB | 1395391 | 5/1975 |
| GB | 1 467 828 | 3/1977 |
| GB | 2145335 A | 3/1985 |
| GB | 2147506 A | 5/1985 |
| GB | 2 164 569 A | 3/1986 |
| GB | 2 267 648 A | 12/1993 |
| JP | 09/216240 A | 8/1997 |
| WO | WO 80/01044 | 5/1980 |
| WO | WO 82/03548 | 10/1982 |
| WO | WO 86/06969 | 12/1986 |
| WO | WO 87/01950 | 4/1987 |
| WO | WO 91/03277 | 3/1991 |
| WO | WO 92/15353 | 9/1992 |
| WO | WO 92/20395 | 11/1992 |
| WO | WO 93/01854 | 2/1993 |
| WO | WO 94/02190 | 2/1994 |
| WO | WO 94/16759 | 8/1994 |
| WO | WO 94/20051 | 9/1994 |
| WO | WO 95/02428 | 1/1995 |
| WO | WO 96/17643 | 6/1996 |
| WO | WO 96/25983 | 8/1996 |
| WO | WO 96/39206 | 12/1996 |
| WO | WO 97/07847 | 3/1997 |
| WO | WO 97/41911 | 11/1997 |
| WO | WO 98/04310 | 2/1998 |
| WO | WO 98/11930 | 3/1998 |
| WO | WO 98/18514 | 5/1998 |
| WO | WO 98/24499 | 6/1998 |
| WO | WO 98/26829 | 6/1998 |
| WO | WO 98/26830 | 6/1998 |
| WO | WO 98/48878 | 11/1998 |
| WO | WO 00/57942 | 10/2000 |

OTHER PUBLICATIONS

Product Brochure for ResMed "Sullivan® Mirage™—The Mirage is Real. A Perfect Fit—First Time,"©1998 ResMed Limited, 4, pages.

Color Photo of "Weinmann Mask" 1998, 1 page.

Mask 1 Photographs, Respironics Inc., Reusable Full Mask (small) Part #452033 Lot #951108.

Mask 2 Photographs, Puritan—Bennett, Adam Curcuit, Shell Part #231700, Swivel Part #616329–00, Pillows (medium) Part #616324.

Mask 3 Photographs, DeVilbiss Healthcare Inc., Devilbiss Seal–Ring and CPAP Mask kit (medium), Part #73510–669.

Mask 4 Photographs, Respironics Inc., Monarch Mini Mask with Pressure Port. Part #572004, Monarch Headgear, Part #572011.

Mask 5 Photographs, Healthdyne Technologies, Nasal CPAP Mask (medium narrow), Part #702510.

Mask 6 Photographs, Healthdyne Technologies, soft Series Nasal CPAP Mask, Part #702020.

Mask 7 Photographs, DeVilbiss Healthcare Inc., Small Mask and Seal Rings, Part #73510–668.

Mask 8 Photographs, Respironics Inc., Reusable Contour Mask (medium), Part #302180.

Mask 9 Photographs, Healthdyne Technologies, Healthdyne Large Headgear.

Mask 10 Photographs, Respironics, Inc., Soft Cap (medium), Part #302142.

Mask 11 Photographs, Weinmann: Hamburg, Nasalmaskensystem mit Schalldämpfer (medium), Part #WN 23105.

Mask 12 Photographs Life Care.

Mask 13 Photographs, Healthdyne Technologies.

Mask 14 Photographs, King System.

Mask 15 Photographs, Respironics Inc., Pediatric Mask.

Mask 16 Photographs, Hans Rudolph Inc., Hans Rudolph Silicone Rubber Face Mask/8900.

* cited by examiner

FOREHEAD SUPPORT FOR A FACIAL MASK

CROSS REFERENCE TO RELATED APPLICATION

This application is a continuation of U.S. application Ser. No. 09/538,349, filed Mar. 29, 2000 now U.S. Pat. No. 6,520,182, now allowed, the specification and drawings of which are incorporated herein by reference.

FIELD OF THE INVENTION

The present invention relates to a forehead support for a facial mask used to supply breathable gas to a wearer's airways.

The invention has been developed primarily for use in supporting a nasal mask used in Continuous Positive Airway Pressure (CPAP) treatment of, for example, Obstructive Sleep Apnea (OSA) and other ventilatory assistance treatments such as Non-Invasive Positive Pressure Ventilation (NIPPV) and will be described hereinafter with reference to this application. However, it will be appreciated that the invention is not limited to these particular uses and is also suitable for use with, for example, full-face (ie. nose and mouth) masks.

BACKGROUND TO THE INVENTION

CPAP treatment is a common ameliorative treatment for breathing disorders including OSA. CPAP treatment, as described in U.S. Pat. No. 4,944,310, provides pressurised air or other breathable gas to the entrance of a patient's airways at a pressure elevated above atmospheric pressure, typically in the range 4–20 cm $H_2O$.

It is also known for the level of treatment pressure to vary during a period of treatment in accordance with patient need, that form of CPAP being known as automatically adjusting nasal CPAP treatment, as described in U.S. Pat. No. 5,245,995.

NIPPV is another form of treatment for breathing disorders which can involve a relatively higher pressure of gas being provided in the patient mask during the inspiratory phase of respiration and a relatively lower pressure or atmospheric pressure being provided in the patient mask during the expiratory phase of respiration.

In other NIPPV modes the pressure can be made to vary in a complex manner throughout the respiratory cycle. For example, the pressure at the mask during inspiration or expiration can be varied through the period of treatment.

Typically, the ventilatory assistance for CPAP or NIPPV treatment is delivered to the patient by way of a nasal mask. Alternatively, a mouth mask or full face mask or nasal prongs can be used. In this specification any reference to a mask is to be understood as incorporating a reference to a nasal mask, mouth mask, full face mask or nasal prongs.

In this specification any reference to CPAP treatment is to be understood as embracing all of the above described forms of ventilatory treatment or assistance.

A CPAP apparatus broadly comprises a flow generator constituted by a continuous source of air or other breathable gas such as a hospital piped supply or a blower. In the latter case, an electric motor drives the blower and is typically controlled by a servo-controller under the control of a microcontroller unit. In either case, the gas supply is connected to a conduit or tube which in turn is connected to a patient nasal or full-face mask which incorporates, or has in close proximity, an exhaust to atmosphere for venting exhaled gases. Examples of prior art nasal masks are shown in U.S. Pat. Nos. 4,782,832 and 5,243,971.

The supply conduit delivers gas into a chamber formed by walls of the mask. The mask is normally secured to the wearer's head by straps. The straps are adjusted to pull the mask against the face with sufficient force to achieve a gas tight seal between the mask and the wearer's face.

A problem that arises with the use of the existing masks is that in order for the straps to be tight, the mask is compressed against the wearer's face and may push unduly hard on the wearer's nose. Additionally, the mask may move around the wearer's face. Thus, there has been hitherto provided a forehead support, which provides a support mechanism between the mask and the forehead. This forehead support prevents both the mask from pushing too strongly against the wearer's nose and/or facial region as well as minimising movement of the mask with the addition of a contact point between the mask and the wearer's head thereby reducing uncomfortable pressure points. Additionally, the forehead support can be arranged to prevent the gas supply conduit from contacting the wearer's forehead or face.

Forehead supports with a single cushion and a single contact point or the forehead are known.

The applicant's U.S. patent application Ser. No. 09/008,708 relates to a substantially rigid one-piece forehead support having a pair of forehead cushions mounted at each outer end of the support. This forehead support is connected to the top of a facial mask and includes an adjustable mechanism to allow the spacing between the top of the facial mask and the forehead support to be altered between predetermined positions to thereby alter the angle of the mask relative to the wearer's head to suit the wearer's facial topography.

It is an object of the present invention to provide an alternate form of forehead support.

SUMMARY OF THE INVENTION

Accordingly, in a first aspect, the present invention provides a forehead support for a respiratory mask, said forehead support including a pair of arms, wherein: the arms are each adapted to locate a forehead cushion; the arms are adapted to pivot relative to each other; and the arms are selectively lockable at two or more angular positions relative to each other.

In a second aspect, the present invention provides a respiratory mask assembly comprising a respiratory mask and a forehead support, said forehead support including a pair of arms, wherein: the arms are each adapted to locate a forehead cushion; the arms are adapted to pivot relative to each other; and the arms are selectively lockable at two or more angular positions relative to each other.

As the angle between the arms adjacent to wearer's forehead is decreased or increased the distance between the forehead and the extension of the respiratory mask is increased or decreased respectively, thereby altering the angle of the respiratory mask relative to the wearer's face.

The arms are preferably also adapted to each pivot relative to the respiratory mask.

Preferably, each of the arms include a cylindrical recess adapted to pivotally receive a cylindrical boss provided on the respiratory mask.

The respiratory mask preferably includes an extension adjacent and above, in use, the wearer's nose on which the cylindrical boss is provided.

Desirably, one of the arms includes a tongue adapted to be received in one of at least two grooves provided on the other of the arms so as to lock the arms at one of two or more predetermined said angular positions.

The tongue is preferably provided on a flexible member which is adapted to permit the tongue be moved out of engagement with the grooves by manual manipulation of the member.

The forehead cushions are desirably located on the outer ends of the arms.

The arms preferably also include means to connect a head strap thereto.

The respiratory mask preferably also includes means to connect a head strap thereto.

BRIEF DESCRIPTION OF THE DRAWINGS

Preferred embodiments of the invention will now be described, by way of examples only, with reference to the accompanying drawings in which.

DETAILED DESCRIPTION OF THE PREFERRED EMBODIMENTS

Figure 1:
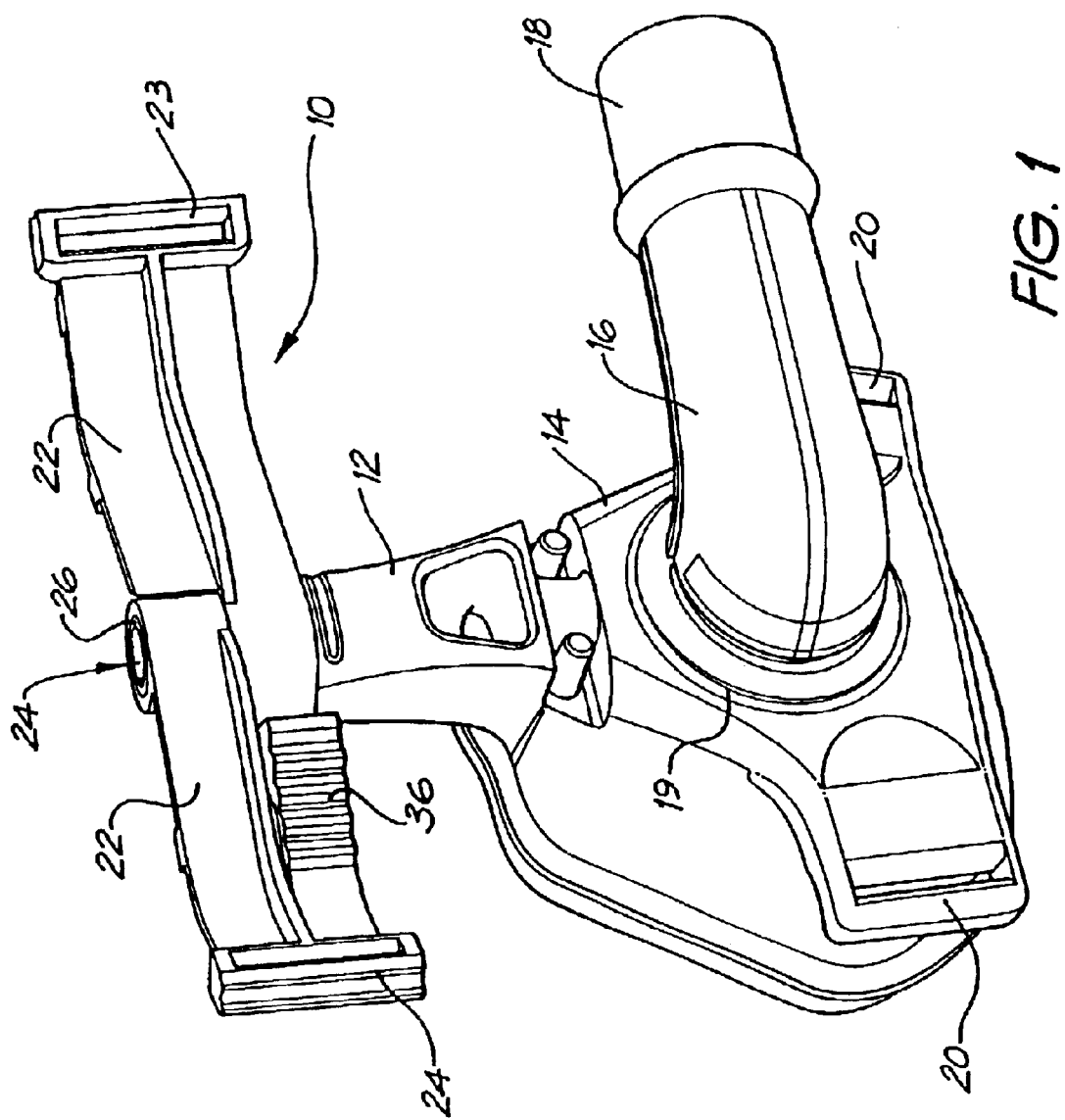
FIG. 1 is a front perspective view of a first embodiment of a forehead support according to the invention connected to a nasal mask.
Figure 2:
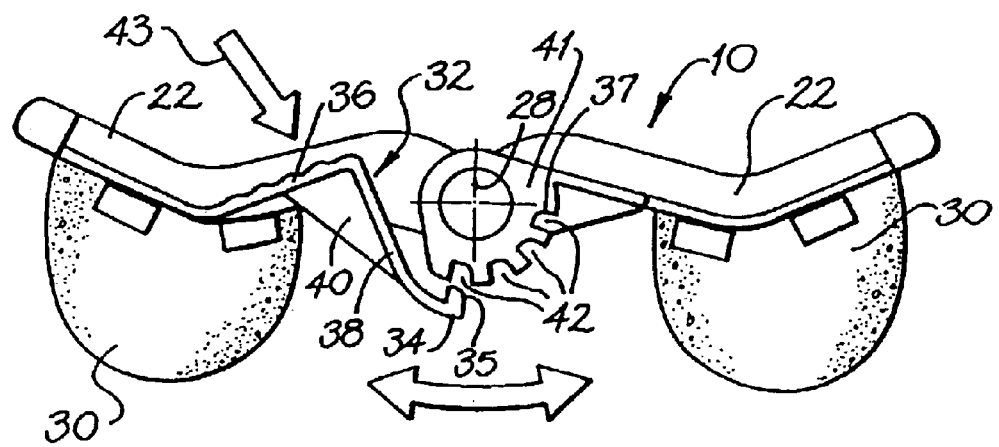
FIG. 2 is an underside view of the forehead support shown in FIG. 1 with the tongue of one arm free of engagement with the grooves of the other arm.
Figure 3:
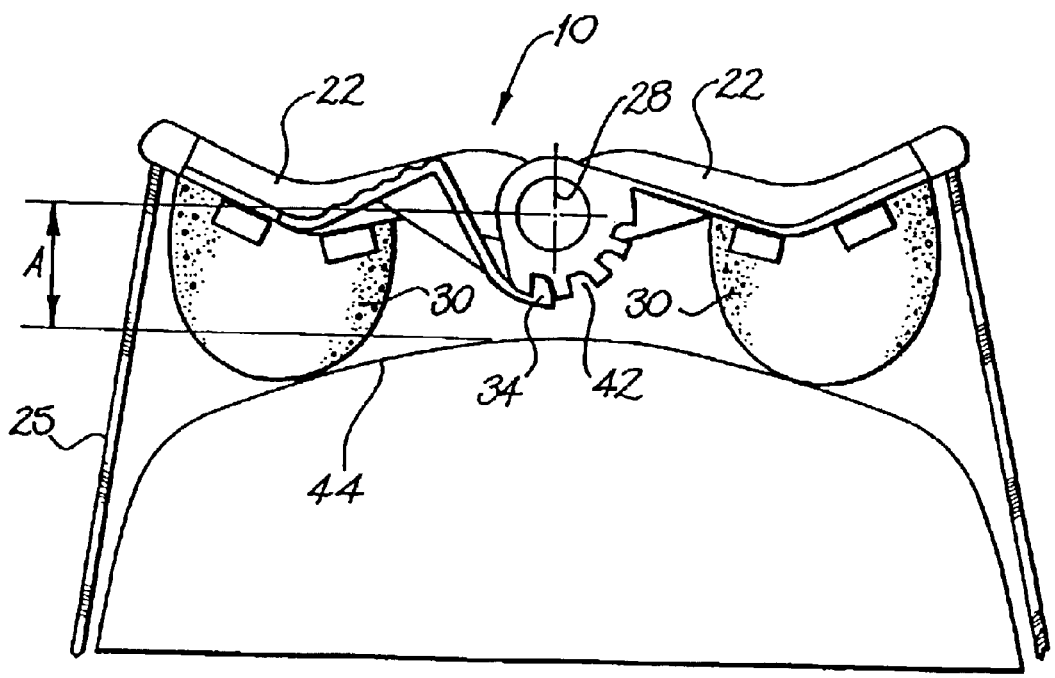
FIG. 3 is an underside view of the forehead support shown in FIG. 1 with the tongue and groove engaged at the first of four positions.
Figure 4:
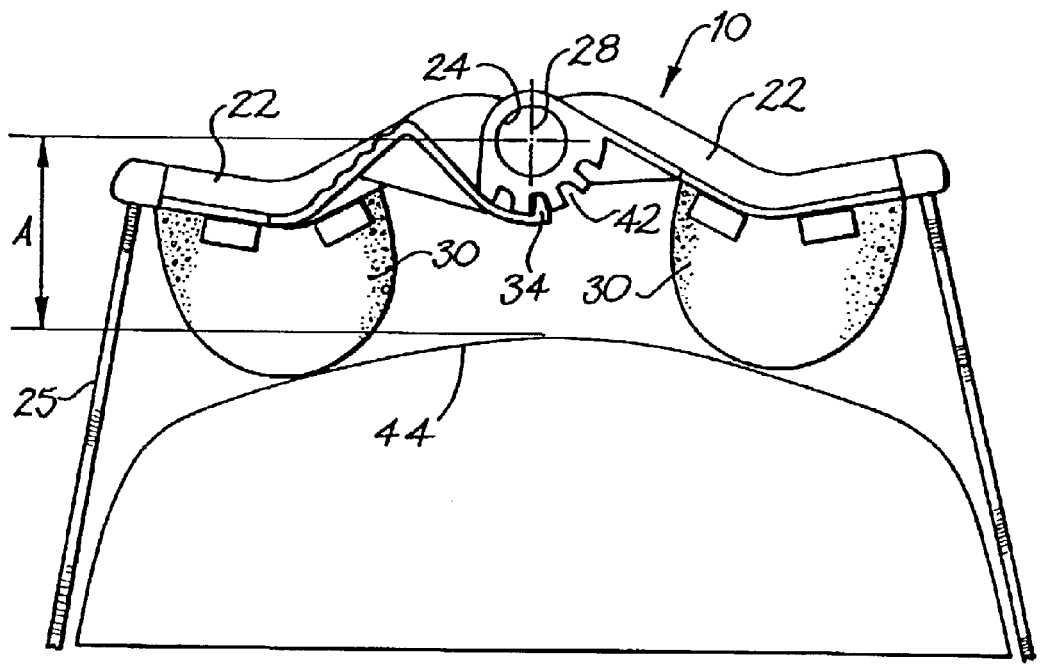
FIG. 4 is an underside view of the forehead support shown in FIG. 1 with the tongue and groove engaged in the second of four positions.
Figure 5:
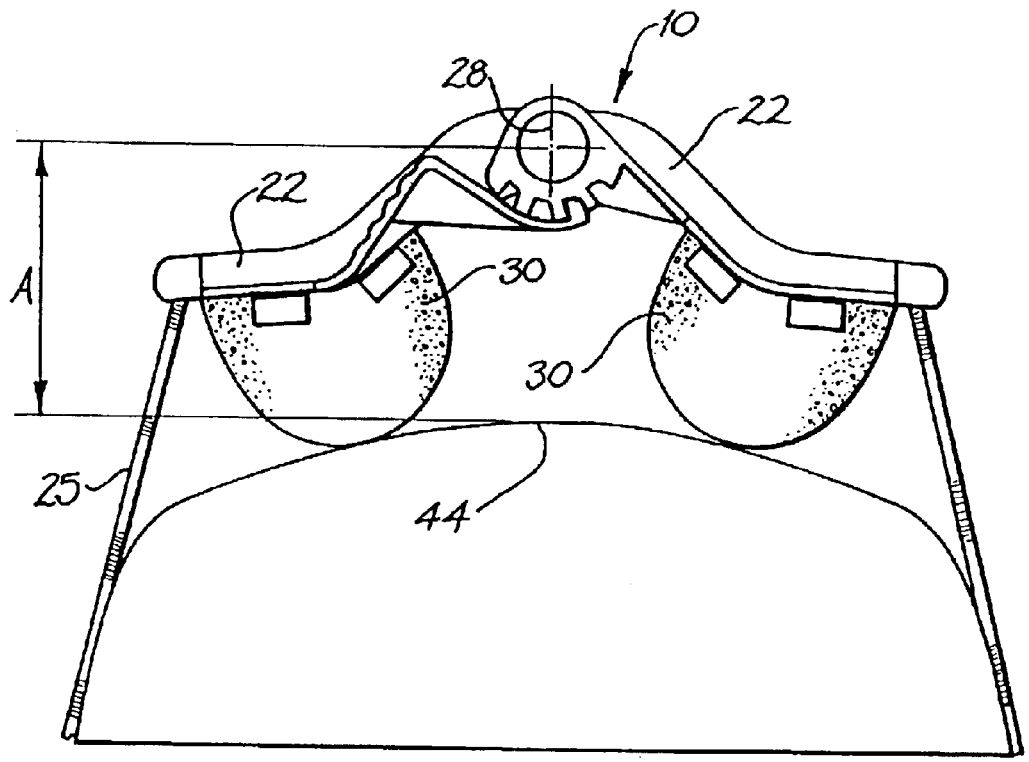
FIG. 5 is an underside view of the forehead support shown in FIG. 1 with the tongue and groove engaged at the third of four positions.
Figure 6:
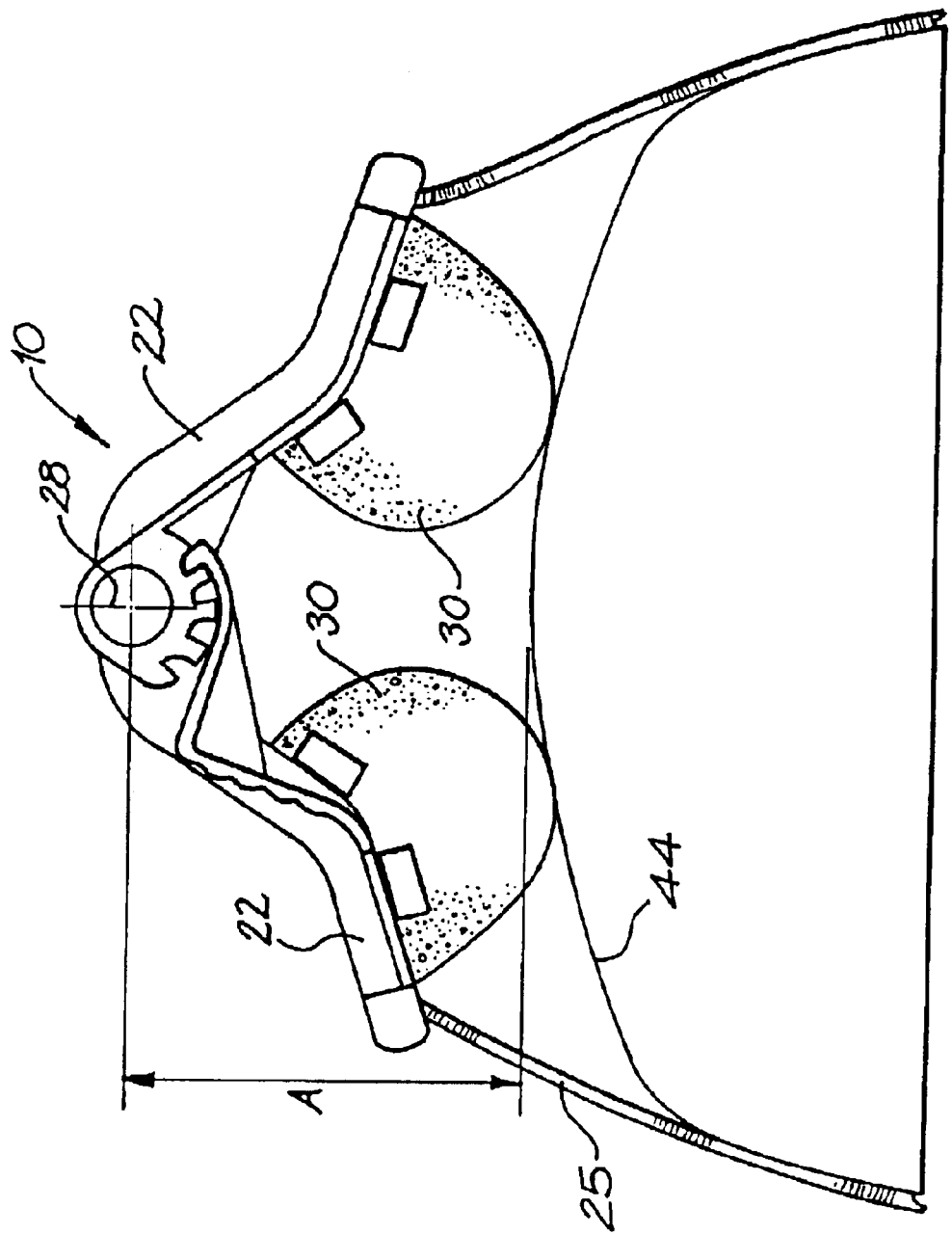
FIG. 6 is an underside view of the forehead support shown in FIG. 1 with the tongue and groove engaged at the fourth of four positions.
Figure 7:
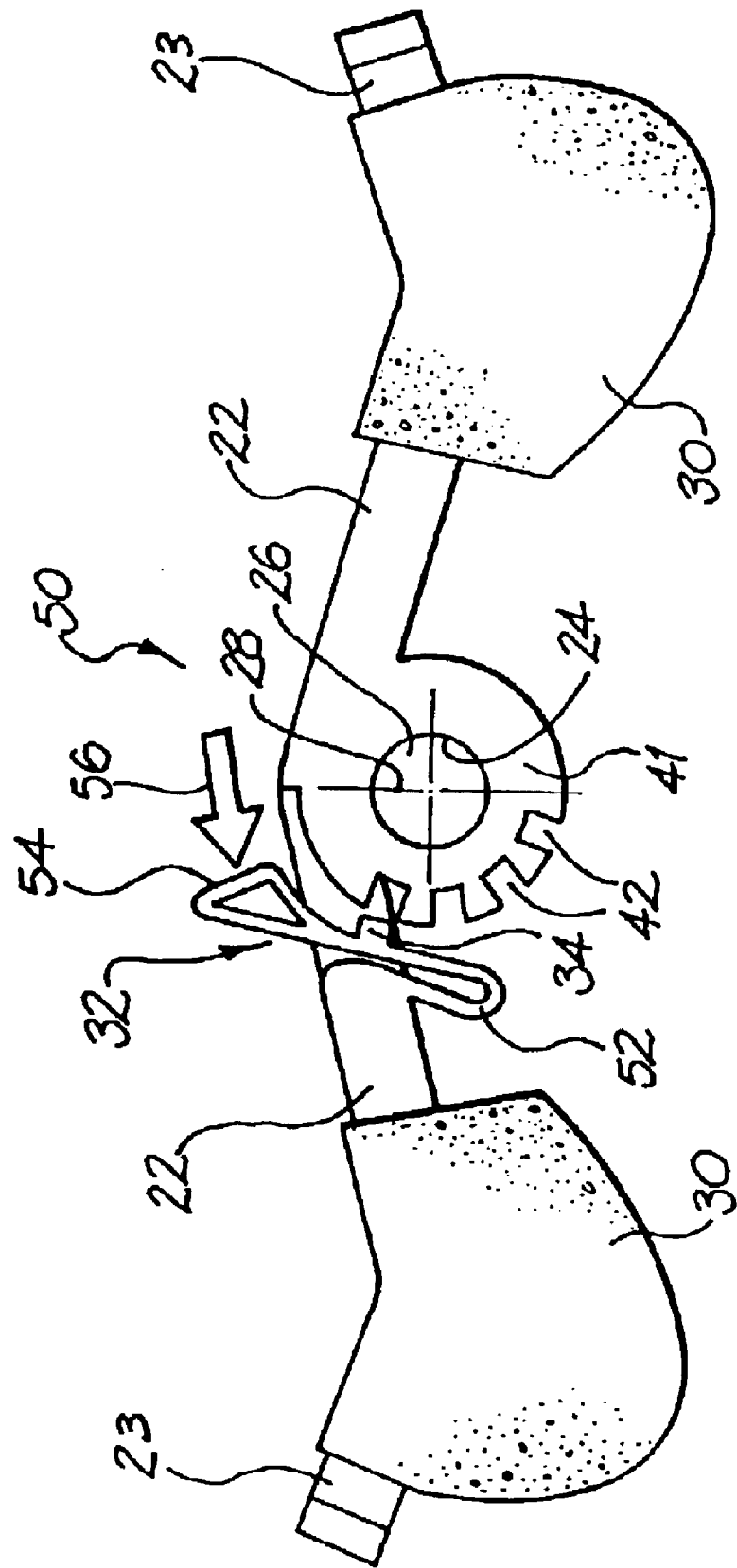
FIG. 7 is an underside view of a second embodiment of the forehead support according to the invention with the tongue of one arm free of engagement with the grooves of the other arm.
Figure 8:
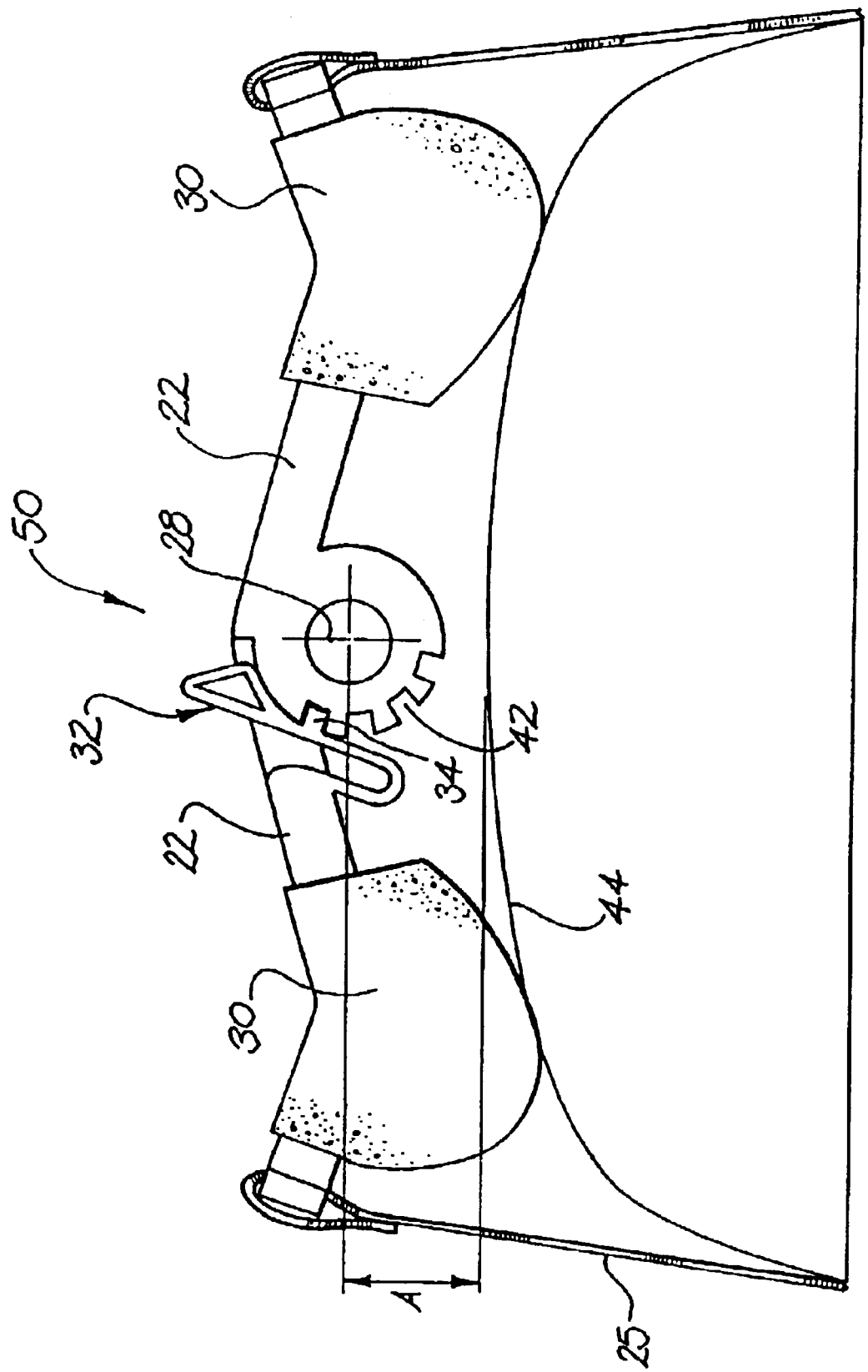
FIG. 8 is an underside view of the forehead support shown in FIG. 7 with the tongue and groove engaged at the first of four positions.
Figure 9:
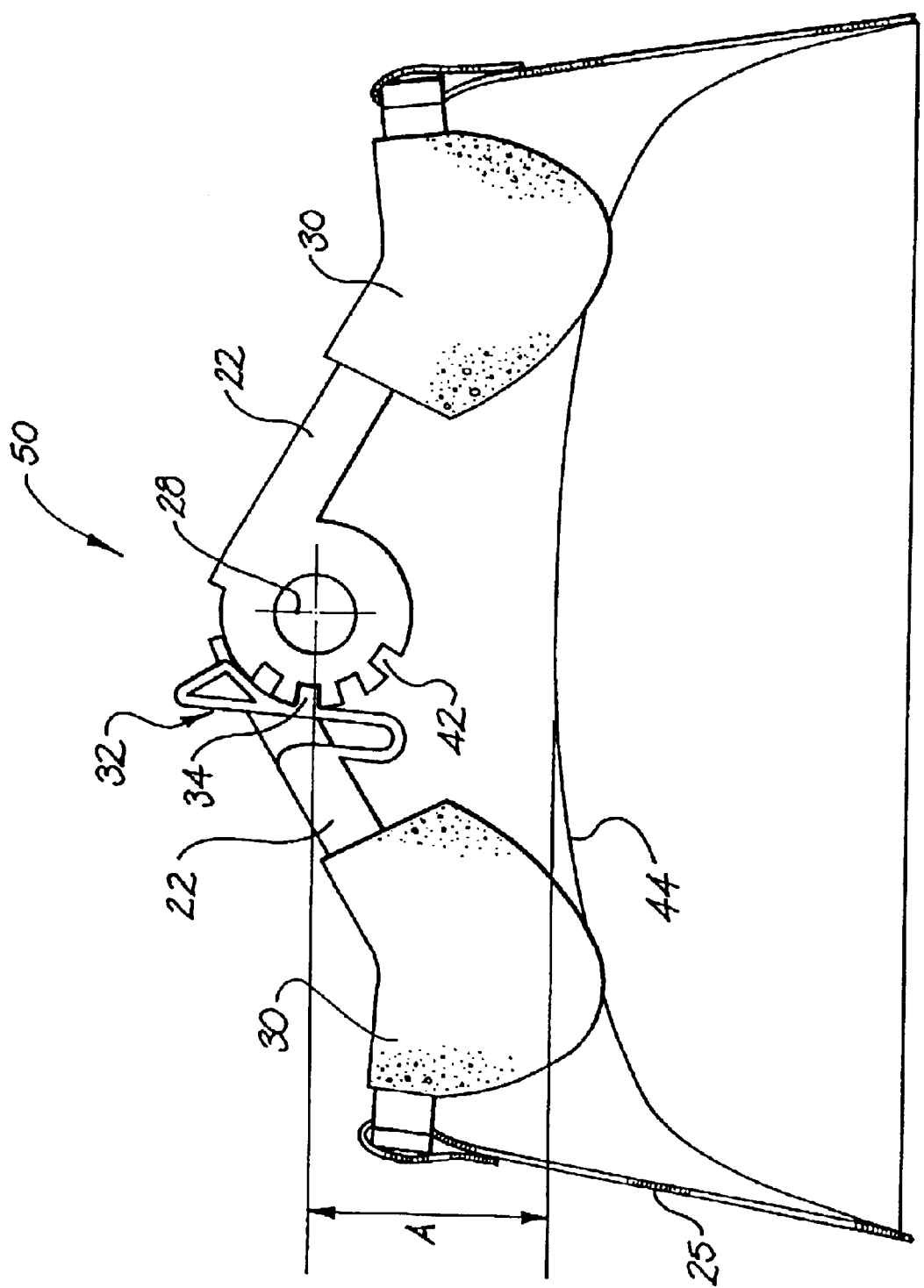
FIG. 9 is an underside view of the forehead support shown in FIG. 7 with the tongue and groove engaged at the second of four positions.
Figure 10:
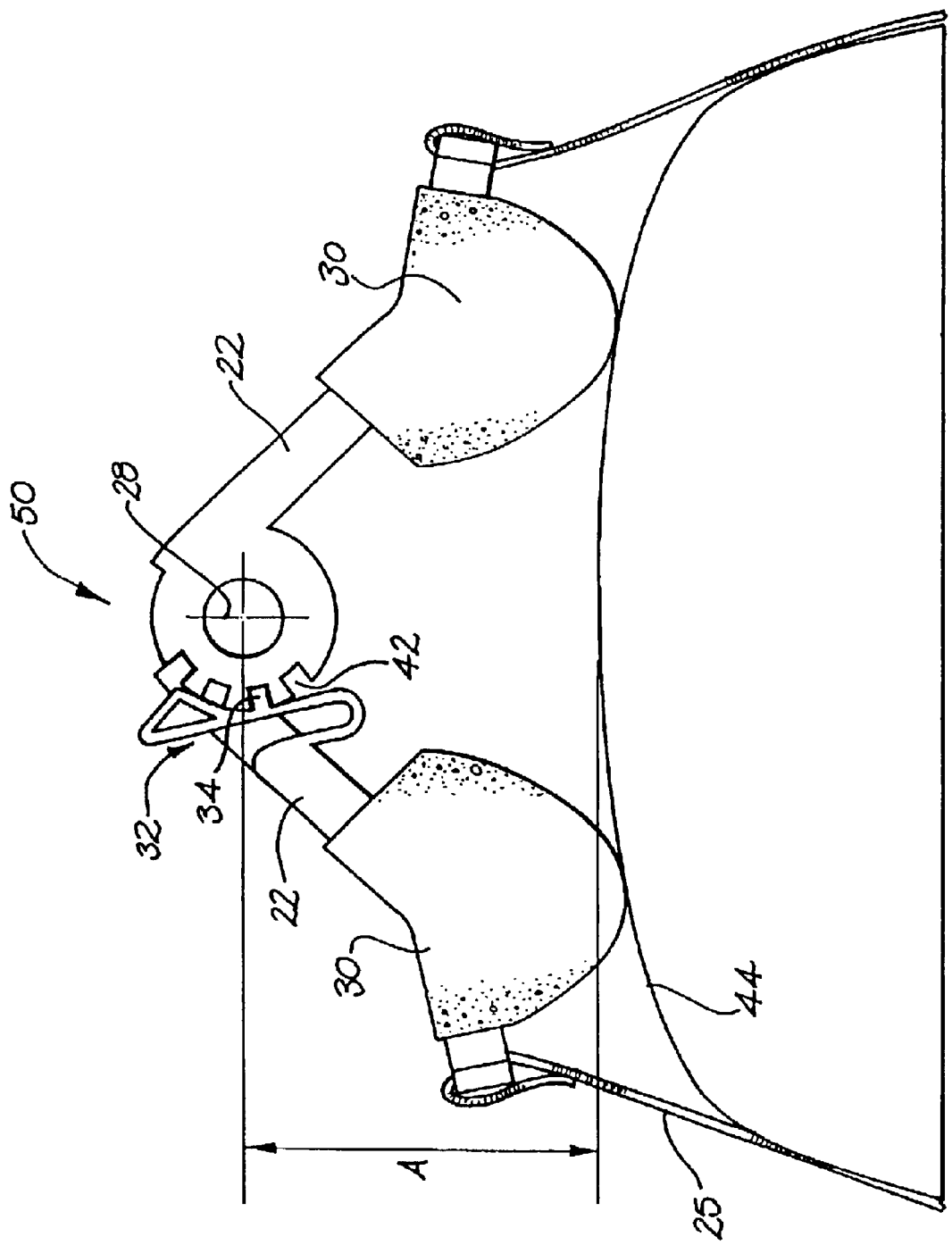
FIG. 10 is an underside view of the forehead support shown in FIG. 7 with the tongue and groove engaged at the third of four positions.
Figure 11:
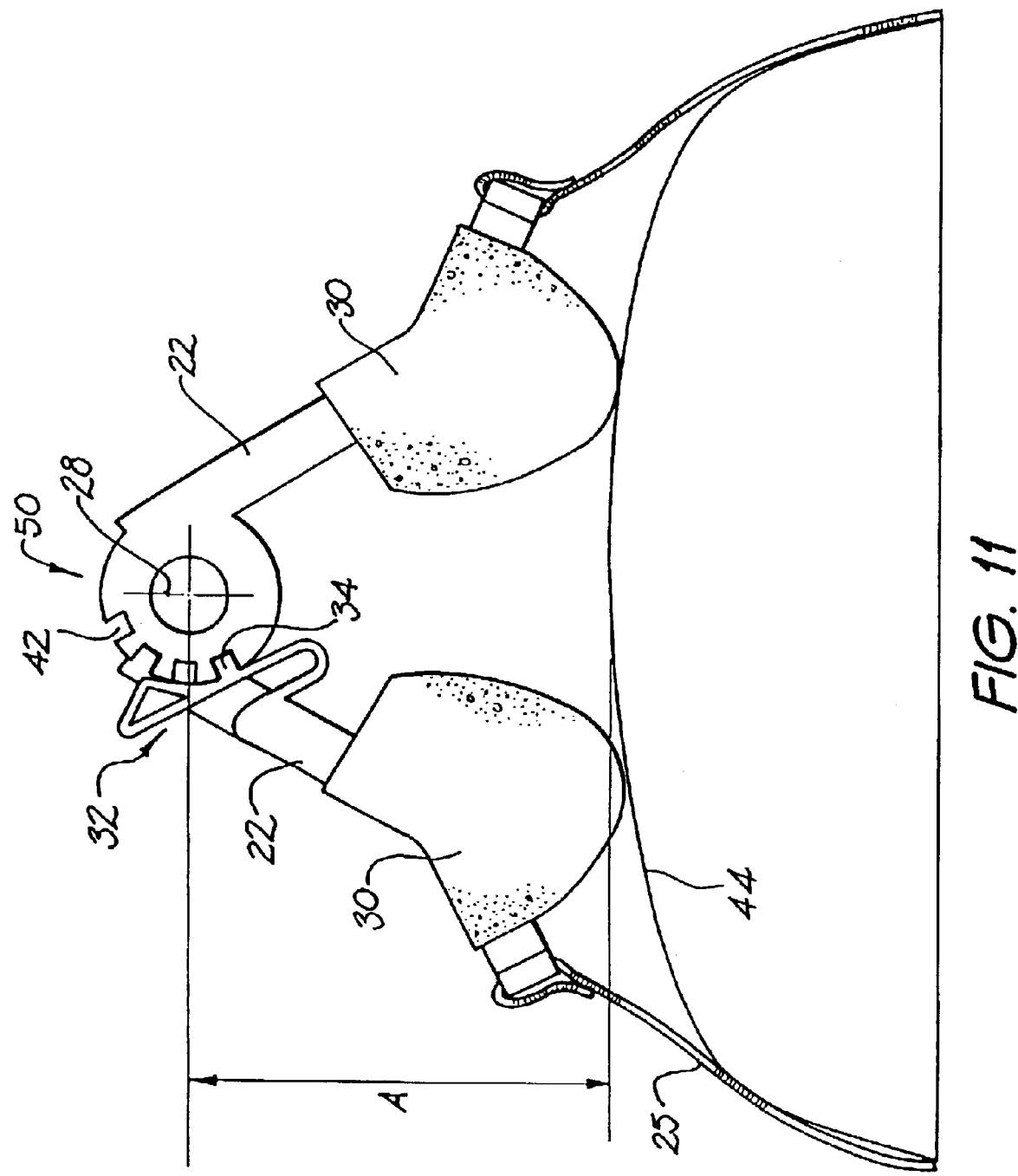
FIG. 11 is an underside view of the forehead support shown in FIG. 7 with the tongue and groove engaged at the fourth of four positions.
Figure 12:
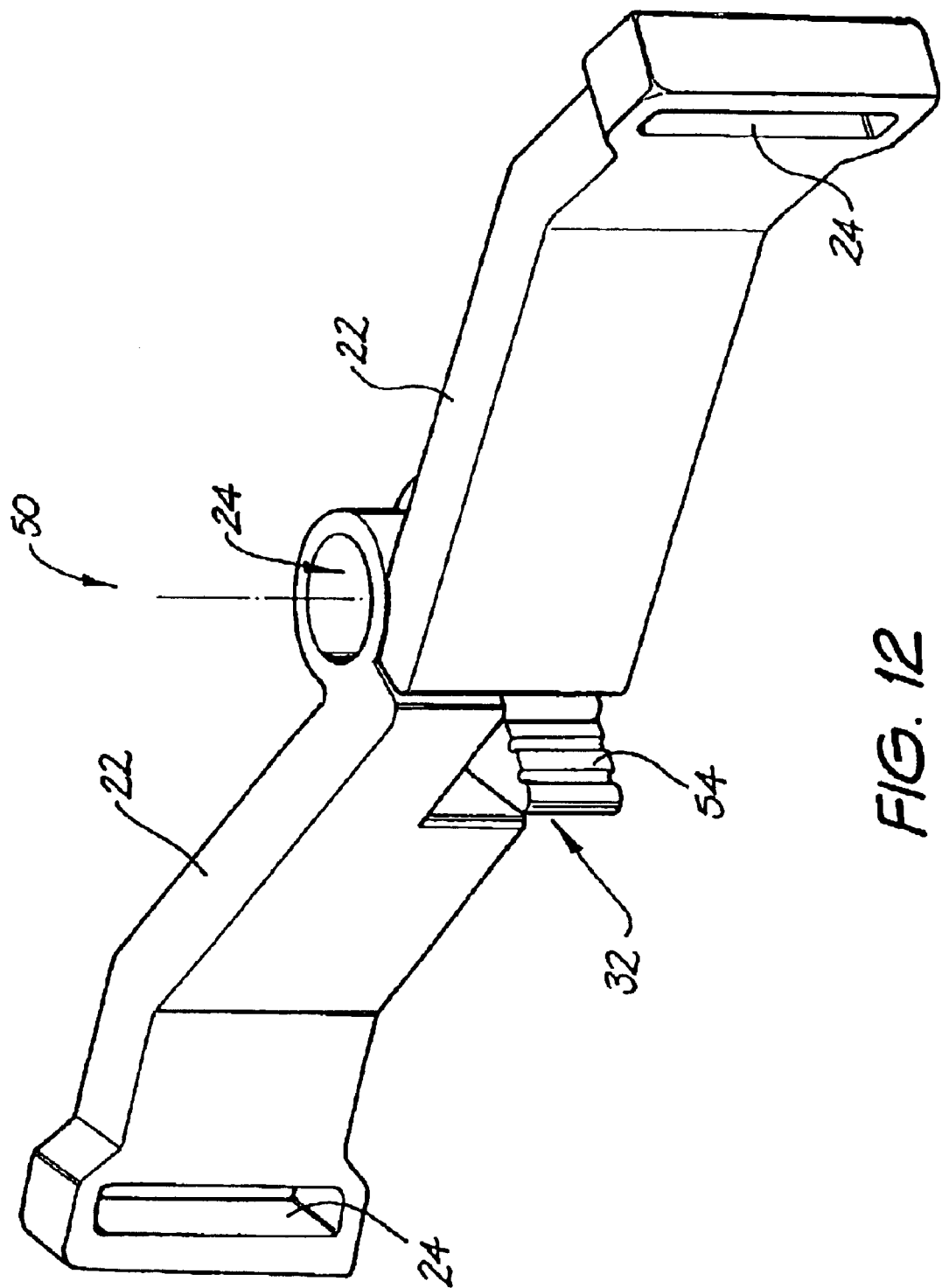
FIG. 12 is an upper perspective view of the forehead support shown in FIG. 7.
Figure 13:
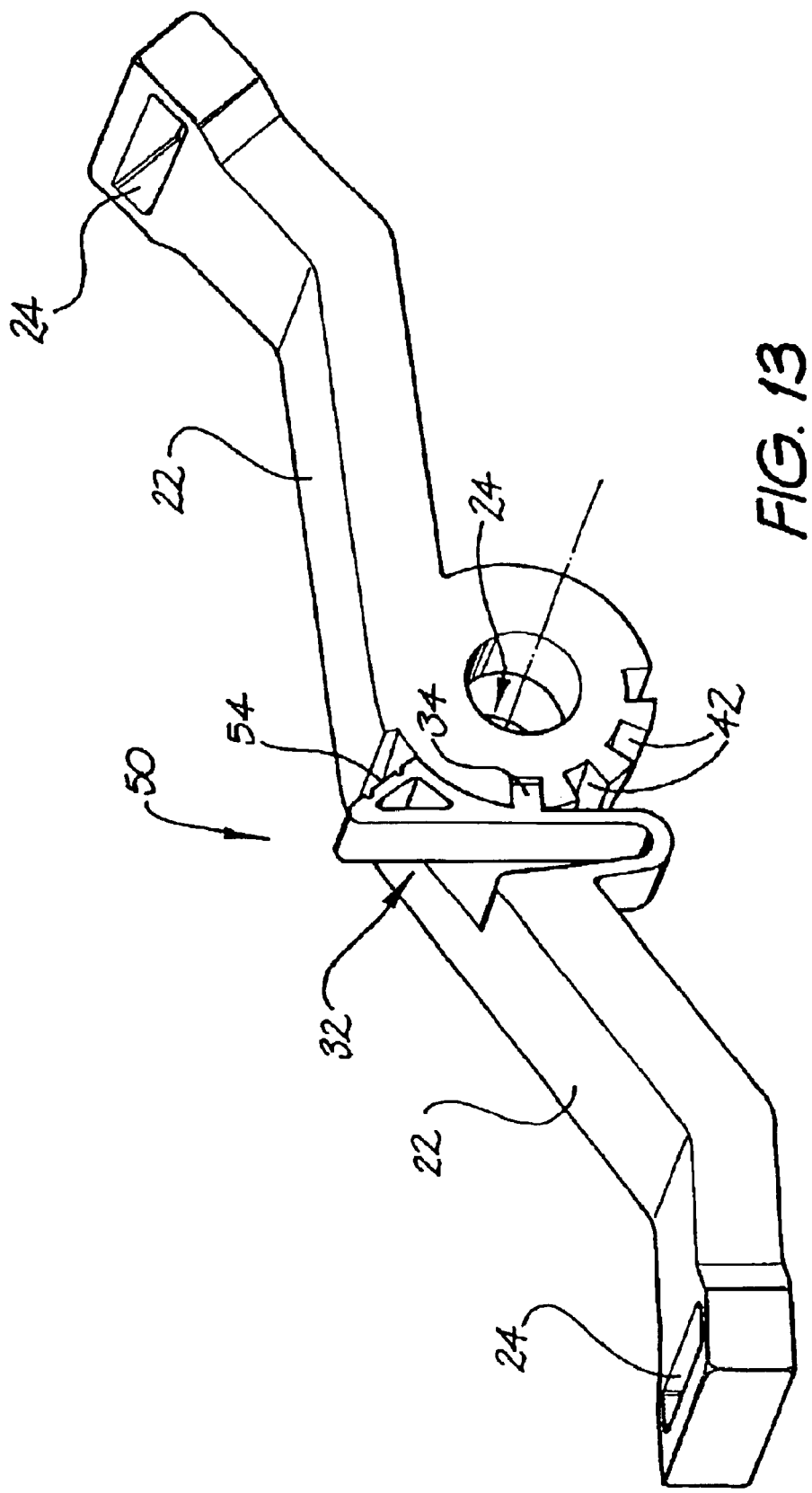
FIG. 13 is an lower perspective view of the forehead support shown in FIG. 7.

FIGS. 1 to 6 show a first embodiment of a forehead support 10 according to the present invention. As shown in FIG. 1, the forehead support 10 is adapted for connection to an extension 12 of a facial respiratory mask 14 used to supply breathable gas to a wearer's airways. The mask 14 includes an angled connector 16 which has a distal end 18 for connection to a gas supply conduit (not shown) and a proximal end 19 for connection to the mask 14. The connector 16 communicates the supplied gas from the gas supply conduit to the interior of the mask 14.

The extension 12 is positioned on top of the nasal mask 14 generally adjacent and above the wearer's nose. It will be appreciated that this is just one example of a facial mask that could be supported by the forehead support 10. For example, the forehead support also finds application in supporting full-face (ie. nose and mouth) masks.

Forehead supports according to the invention can also be used with facial masks in which the gas supply connector 16 is incorporated into the mask in the general position of the extension 12. In this type of mask, the supplied gas flows through or past the forehead support 12.

The mask 14 includes a pair of slotted connectors 20 to which are respectively connected ends of a lower head strap (not shown) for securing the nasal mask to the wearer's head.

The forehead support 10 includes a pair of arms 22 pivotally mounted to each other adjacent the extension 12. Each of the arms 22 includes a slotted connector 23 to which ends of an upper head strap 25 are respectively connected (see FIGS. 3 to 6).

The arms 22 each include a cylindrical recess 24 which receives a cylindrical boss 26 provided on the extension 12. As best shown in FIGS. 2 to 6, the cylindrical recess 24 and boss 26 allow the arms 22 to pivot relative to each other, and the extension 12 (and thus the mask 14), about axis 28. These figures also show the forehead support cushions 30 that are mounted at the ends of each of the arms 22. Examples of cushions 30 include solid foam sponges, silicone, stuffed pads, dual durometer foams, single pads or multiple pads joined together. The cushions 30 can be integrally moulded with the arms 22 or attached thereto by clips or adhesives or the like.

Also as shown in FIGS. 2 to 6, the right hand side arm 22 (shown on the left hand side as FIGS. 2 to 6 are underside views) includes a flexible member 32 which has a tongue 34 on its distal end. The member 32 has a first part 36 and a second part 38 which are bridged by a brace 40. The left hand side arm includes a generally arcuate shaped boss 41 having four grooves 42. It will be appreciated that four grooves is merely preferable and that only two or more grooves are required. It will also be appreciated that the flexible member 32 can be on the left hand side arm 22 and the boss 41 can be on the right hand side arm 22.

The arms are constructed from a plastics material, such as polycarbonate, which allows the member 32, when pressed in the general direction of arrow 43, to be flexed relative to the arm 22 upon which it is mounted to release the tongue 34 from engagement from one of the grooves 42 to allow angular adjustment between the arms 22. Releasing the member 32 biases the tongue 34 towards the grooves 42. When the tongue 34 and one of the grooves 42 are aligned, as is shown in FIGS. 3 to 6, the tongue 34 engages one of the grooves 42. When the tongue 34 is engaged with one of the grooves, the arms 22 are locked against pivotal movement therebetween at a predetermined angle.

The tongue 34 has a radiused leading corner 35 and a similar radius is provided on the corresponding corner 37 of each of the grooves. The leading corner 35 and corresponding corners 37 can also be angled. When the arms 22 are pushed towards each other in a direction reducing the angle therebetween, the corner 35 causes the tongue 34 to ride up out of engagement with the slot and fall into engagement with the next slot. This allows the angle between the arms 22 to be quickly adjusted in a ratchet type fashion.

FIGS. 3 to 6 respectively show the tongue 34 engaged in the first, second, third and fourth of the four grooves 42. These figures also show a forehead represented by line 44. The distance between the front of the forehead 44 and the axis 28 is indicated by the distance A. FIGS. 3 to 6 show that the distance A increases or decreases as the angle between the arms 22 adjacent the forehead 44 is decreased or increased respectively.

The extension 12 of the nasal mask 14 is connected to the forehead support 10 generally in the region of the axis 28. Consequently, as the arms are pivoted towards each other the distance A is increased. This suits wearers with relatively high nasal regions and relatively low foreheads. Conversely, as the arms 22 are pivoted away from each other the distance A is decreased. This suits wearers with relatively low nasal regions and relatively high foreheads.

In this way the forehead support 10 advantageously allows the mask 14 to be positioned to comfortably suit the particular topography of the wearer's face by adjusting the angle of tilt of the mask 14 relative to the wearer's face. As examples, the position of arms 22 in FIG. 3 would be more suitable for use with a wearer having a protruding or bulbous forehead whilst the position of the arms 22 in FIG. 6 would be more suitable for use with a wearer having a shallow forehead or protruding cheeks or nose.

The curved shape of the cushions 30 allows them to effectively "roll" over the wearer's forehead during angular adjustment of the arms 22.

Further, as the arms 22 can also pivot relative to the mask 14, then the forehead support 10 is also able to better fit wearers whose foreheads are not symmetrical about the front-to-rear centreline of their head.

Further, the forehead support advantageously allows the angle between the arms to be adjusted using only one hand. The ease of adjustment of the arms also makes the forehead support particularly suitable for use by sick, weak or one-armed wearers.

FIGS. 7 to 13 shown a second embodiment of a forehead support 50 according to the present invention. Like reference numerals to those used in describing the first embodiment will be used to indicate like features in the second embodiment.

The forehead support 50 is similar to the forehead support 10 shown in FIGS. 1 to 6 except the flexible member 32 is mounted to the right hand arm 22 and has a cantilever configuration. To increase resilience, the member 32 is bent back on itself into a U-shaped configuration to resiliently bias it against the boss 41 provided on the left arm 22. The member 32 also includes a protruding portion 54 which, when pressed in the general direction of arrow 56, causes the tongue 34 to move out of engagement with one of the grooves 42 to allow angular adjustment between the arms 22. Releasing the member 32 biases the tongue 34 towards the grooves 42. Engagement between the tongue 34 and one of the grooves 42 occurs when they are aligned.

Although the invention has been described with reference to a specific example, it will be appreciated by those skilled in the art that the invention may be embodied in many other forms.

As an example, the forehead support can include means to resiliently bias the arms relative to one another such that they increase or decrease their angle relative to one another when the tongue is disengaged from one of the slots. Also, in the embodiments described above the angle between the arms can be changed independently of the angle between the mask and the arms. However, in an alternative embodiment, the arms can be adapted to simultaneously change their relative angle, thereby maintaining a symmetrical position relative to the mask. Further, the tongue and grooves of the second embodiment can have the radiused corners of the first embodiment.

I claim:

1. A forehead support for a respiratory mask, said forehead support including a pair of arms, wherein: the arms are each adapted to locate a forehead cushion; the arms are adapted to pivot relative to each other; and the arms are selectively lockable at two or more angular positions relative to each other, wherein each arm includes a base structure configured for coupling with a frame of a respiratory mask.

2. The forehead support as claimed in claim 1, wherein the arms are also adapted to each pivot relative to the respiratory mask.

3. The forehead support as claimed in claim 1, wherein each of the arms include a cylindrical recess adapted to pivotally receive a cylindrical boss provided on the respiratory mask.

4. The forehead support as claimed in claim 1, wherein one of the arms includes a tongue adapted to be received in one of at least two grooves provided on the other arm so as to lock the arms at one of two or more predetermined said angular positions.

5. The forehead support as claimed in claim 4, wherein the tongue is provided on a flexible member which is adapted to permit the tongue to be moved out of engagement with the grooves by manual manipulation of the member.

6. The forehead support as claimed in claim 1, further comprising forehead cushions located on the outer ends of the arms.

7. The forehead support as claimed in claim 1, wherein the arms also include means to connect a head strap thereto.

8. A forehead support as claimed in claim 1, wherein the forehead cushions have a curved shape which allows them to roll over the wearer's forehead during angular adjustment of the arms.

9. The forehead support as claimed in claim 1, wherein each of the arms includes first and second lateral ends, the respective first lateral ends being juxtaposed adjacent one another and the second lateral ends being positioned remote from one another when the arms are positioned in the two or more angular positions.

10. The forehead support as claimed in claim 9, wherein the first lateral ends are positioned adjacent a pivoting portion of the forehead support.

11. The forehead support as claimed in claim 1, further comprising one said forehead cushion positioned between each pair of first and second lateral ends.

12. A forehead support for a mask comprising a pair of arms each having a first end and a second end, wherein the arms have a forehead cushion substantially at each respective first end, wherein the arms are constructed and arranged to pivot with respect to one another about the respective second ends between a first angular position relative to one another and a second angular position relative to one another, wherein the forehead cushions have a curved shape which allows them to roll over the wearer's forehead during angular adjustment of the arms, and wherein each arm includes a base structure configured for coupling with a frame of a respiratory mask.

13. A forehead support as claimed in claim 12, further comprising a locking mechanism constructed and arranged to lock the arms at an angular position relative to one another.

14. A forehead support as claimed in claim 12, wherein the forehead cushions are spaced a distance apart and the distance between the forehead cushions is adjustable by changing an angular position of the first arm relative to the second arm.

15. The forehead support as claimed in claim 12, wherein each of the arms includes first and second lateral ends, the respective first lateral ends being juxtaposed adjacent one another and the second lateral ends being positioned remote from one another when the arms are positioned in the first and second angular positions.

* * * * *